United States Patent
Stoughton

(10) Patent No.: US 6,313,547 B1
(45) Date of Patent: Nov. 6, 2001

(54) APPARATUS FOR QUALITY CONTROL VERIFICATION OF AN ELECTROCHEMISTRY TEST

(75) Inventor: John W. Stoughton, Indianapolis, IN (US)

(73) Assignee: UMM Electronics, Inc., Indianapolis, IN (US)

( * ) Notice: Subject to any disclaimer, the term of this patent is extended or adjusted under 35 U.S.C. 154(b) by 0 days.

(21) Appl. No.: 09/522,136

(22) Filed: Mar. 9, 2000

(51) Int. Cl.[7] .................................................. H02J 1/00
(52) U.S. Cl. .................................................. 307/15; 307/36
(58) Field of Search .................................. 323/267, 364, 323/365, 367; 307/15, 36

(56) References Cited

U.S. PATENT DOCUMENTS

| | | | |
|---|---|---|---|
| 3,967,133 | * 6/1976 | Bokern | 307/10.1 |
| 5,296,817 | 3/1994 | Bills et al. | 324/460 |
| 5,399,256 | 3/1995 | Bohs et al. | 204/409 |
| 5,419,826 | 5/1995 | Zirino | 204/416 |
| 5,511,408 | 4/1996 | Yoshioka et al. | 73/1 R |
| 5,571,396 | 11/1996 | Cormier et al. | 204/418 |
| 5,833,925 | 11/1998 | Shu et al. | 200/63 |
| 5,891,398 | 4/1999 | Lewis et al. | 422/82.02 |

* cited by examiner

Primary Examiner—Shawn Riley
(74) Attorney, Agent, or Firm—Woodard, Emhardt, Naughton, Moriarty & McNett

(57) ABSTRACT

The present invention relates to a dry control cartridge for providing a plurality of voltage and impedance inputs to an electrochemical analysis instrument for verification of its proper functioning. The dry control cartridge includes a battery and a plurality of electrical circuits for providing a plurality of predetermined voltage and impedance outputs. The dry control cartridge is adapted for insertion into an electrochemical analysis device using probe electrodes to measure microvolt-range potential differences, appropriate to the input ranges inherent in the instrument. By comparing the measured voltage and impedance inputs to the predetermined outputs of the cartridge, verification of the instrument's proper functioning and accuracy may be made.

16 Claims, 3 Drawing Sheets

APPARATUS FOR QUALITY CONTROL VERIFICATION OF AN ELECTROCHEMISTRY TEST

TECHNICAL FIELD OF THE INVENTION

The present invention relates generally to electrochemistry and, more particularly, to an apparatus for automatically providing a plurality of standard reference impedance and voltage values to an electrochemistry analysis device.

BACKGROUND OF THE INVENTION

Electrochemical analysis techniques are commonly used to generate medical data about biological fluids, such as blood and urine. Most electrochemical analyses of biological fluids are currently performed away from the patient care site at specialized analytical laboratories. The analytical process usually consists of the physician drawing one biological fluid sample from the patient for each test desired, sending the samples away to a centralized location for analysis, and waiting for the results to come back. The process is expensive, time consuming, and prone to communications error since both the sample and the results have to pass through several different people. Moreover, many samples have short shelf lives necessitating a rushed turn-around time that can foster mistakes. A delay in processing the sample might mean having to draw yet another sample from the patient. Further, it is advantageous to the patient that the test results are obtained as quickly as possible, since the patient can begin receiving treatment only after his condition has been properly diagnosed.

One alternative to sending fluid samples away for electrochemical analysis has been developed in the form of the automatic field analysis unit. A number of miniature field analysis units for automatically conducting electrochemical tests on biological fluids are known, such as those described in the claims and specifications of U.S. patent application Ser. No. 09/248,607 for a "Cartridge-Based Analytical Instrument with Optical Detector", U.S. patent application Ser. No. 09/248,614 for a "Cartridge-Based Analytical Instrument with Rotor Balance and Cartridge Lock/Ejection System", and U.S. patent application Ser. No. 09/248,737 for a "Cartridge-Based Analytical Instrument Using Centrifugal Force/Pressure for Mechanical Transport of Fluids". Typically, such miniature electrochemical testing units include disposable electrochemical test cells or cartridges in which two electrolytic solutions are connected by a salt bridge. One electrolytic solution is a reference solution while the other is the fluid sample to be analyzed. Probe electrodes connected to an electronic controller are introduced into the solutions and the electrical potential therebetween is measured.

It is important that the electrochemical data so generated by the analysis unit be accurate, since it will be used as the basis of a medical diagnosis. To this end, the analysis unit requires regular verification of its testing functions. The electrochemical testing function of the instrument may be checked by inserting a control cartridge containing standardized analytes having a known potential difference. This type of verification of function is known as testing with wet controls or wet testing. While wet controls offer an accurate measure of proper systems operation, they are inconvenient, expensive, and have limited reuse potential.

Another known way of verifying electrochemical function of the instrument is by inserting a control cartridge containing a battery and an electrical circuit to offer a predetermined voltage to the test probe electrodes of the analysis device. This type of verification of function is known as testing with dry controls or dry testing. While dry testing constitutes a quick and convenient one-point test, it is less effective than a test that exercises the instrument across a wide range of input conditions. There is therefore a need for a fast, convenient, inexpensive, and reusable test cartridge capable of providing a range of input voltage conditions to an automated electrochemical analysis instrument for verification of electrochemical testing functions. A means for satisfying this need has so far eluded those skilled in the art.

SUMMARY OF THE INVENTION

The present invention relates to a dry control cartridge for providing a plurality of voltage and impedance inputs to an electrochemical analysis instrument. The cartridge includes a battery and a plurality of electrical circuits for providing a plurality of predetermined voltage and impedance outputs. The cartridge is adapted for insertion into an electrochemical analysis device using probe electrodes to measure electrochemical potential differences. The cartridge is further adapted to provide voltage and impedance outputs appropriate to the input ranges inherent in the instrument. By comparing the measured voltage and impedance inputs to the predetermined outputs of the cartridge, verification of the instrument's accuracy may be made.

One form of the present invention relates to an electrochemical dry control cartridge including a battery, a plurality of circuits, and a connector. The cartridge is adapted to be operationally connected to the probe electrodes of an electrochemical analysis instrument, such that the connector is in electrical communication with the probe electrodes. The cartridge may provide a plurality of predetermined voltage and impedance outputs to the instrument to verify its analytical accuracy.

One object of the present invention is to provide an dry control cartridge for verification of the accurate functioning of an electrochemical analysis instrument. Related objects and advantages of the present invention will be apparent from the following description.

DETAILED DESCRIPTION OF THE PREFERRED EMBODIMENT

Figure 1:
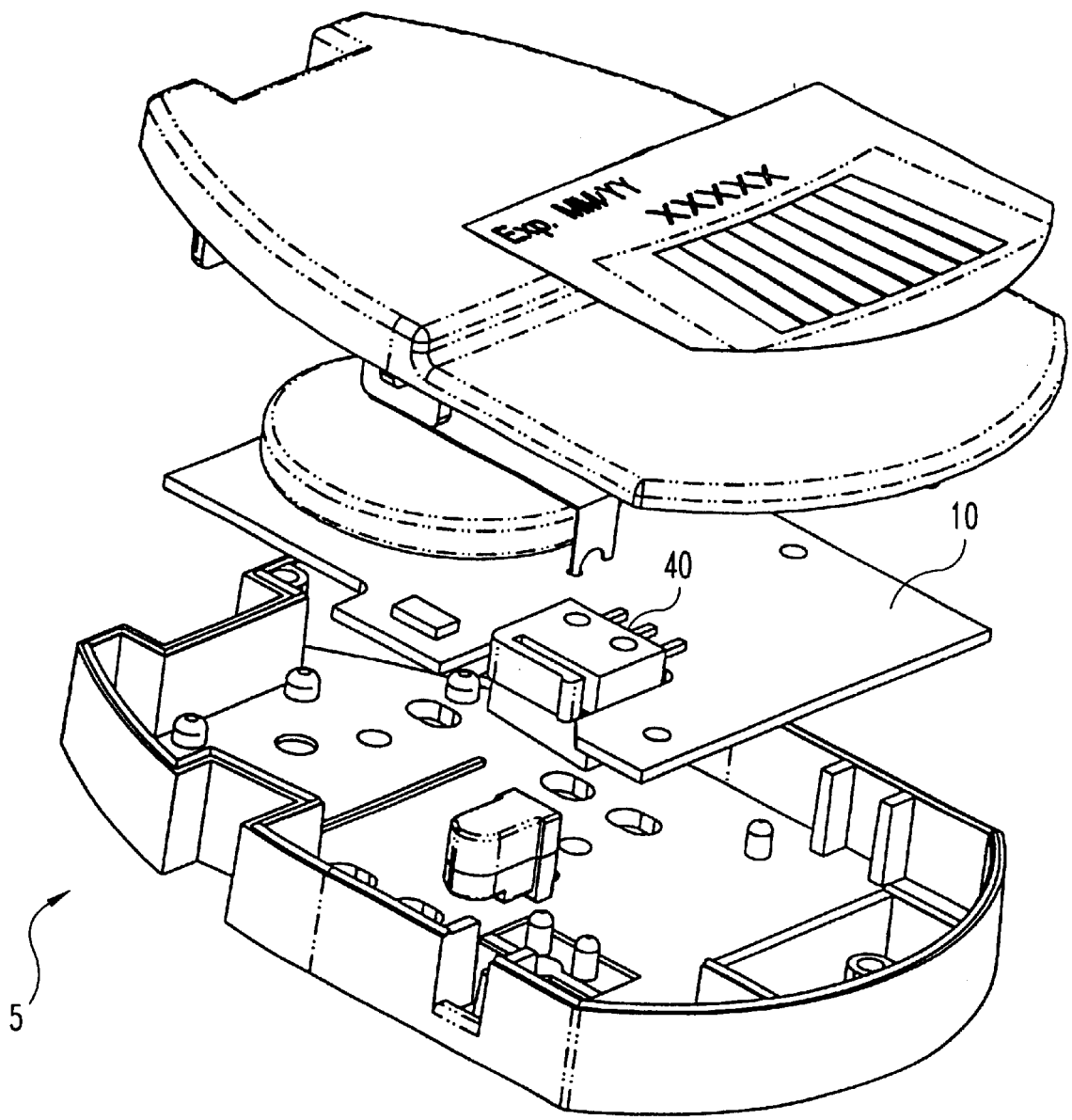
FIG. 1 is an exploded perspective view of a first embodiment dry control cartridge of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Background of Electrochemical Measurement

A typical portable electrochemistry analysis instrument is an automated diagnostic tool adapted for use at a patient treatment site, such as a doctor's office or clinic. The typical portable electrochemistry analysis instrument includes a power source (such as a battery), a carousel for holding a plurality of disposable test cartridges, an electrode assembly for measuring electrical potentials within the test cartridges, a rotor for turning the carousel to sequentially introduce the test cartridges to the electrode assembly, and a controller for tracking the test cartridges, collecting the raw data, and generating, coordinating, and storing data points. The instrument can perform electrochemical analyses on stationary test cartridges by introducing the electrode assembly into the test cartridge and measuring the electric potentials and impedances of the cartridge containing an electrolytic test fluid and a reference standard electrolytic solution housed therein in electric communication. The test cartridges are typically disposable and pre-loaded with everything required for the test except the fluid sample upon which the desired tests are to be performed.

As multiple tests are performed, the electrodes may become contaminated by electrolytes or dirt adhering to the surface. Such contaminants can contribute to erroneous electric potential and/or impedance measurements. Also, in the case of battery operated instruments, as the battery is drained the current and voltage outputs may change, also contributing to measurement errors. Therefore, it is important to periodically check the accuracy of the instrument.

The present invention relates to a dry control cartridge for providing a plurality of discrete voltage and impedance values for use in the verification of the proper functioning of an electrochemical analysis instrument. FIG. 1 illustrates one embodiment of the present invention, a dry control cartridge 5 containing electric circuit 10 adapted to provide a plurality of predetermined voltage and impedance outputs.

Circuit Overview

Figure 2:
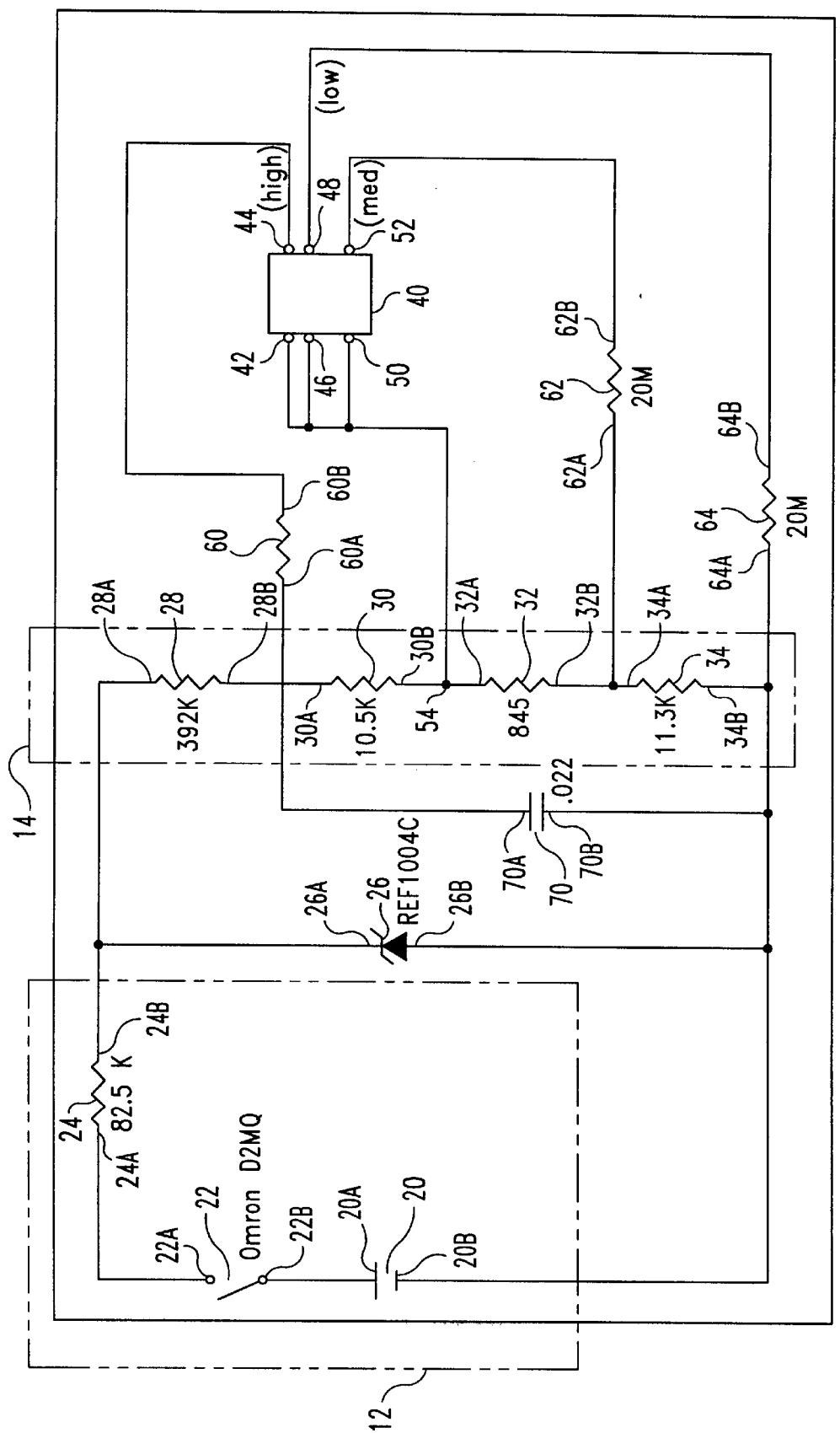
FIG. 2 is a schematic illustration of an electrical circuit contained in the dry control cartridge embodiment of FIG. 1.

Circuit 10 is illustrated schematically in FIG. 2. In a preferred embodiment, circuit 10 includes a power source assembly 12 connected in series to a resistor set 14, each resistor having a predetermined resistance value. Power source assembly 12 preferably includes a battery 20 as a DC power supply, a switch 22, and a resistor 24 connected in series, although in other contemplated embodiments DC power may be supplied by a rectified AC source. As most electrochemical measurements are made in the millivolt range, the voltage supplied by power source assembly 12 may be dropped into the millivolt range by resistor 24 electrically connected in series to battery 20. A diode 26 may also be electrically connected in parallel with power source assembly 12 to insure the provision of a stable reference voltage from which tap voltages may be derived.

In the present embodiment, power source assembly 12 is connected in series to resistor set 14, which includes resistors 28, 30, 32, and 34. As current flows from battery 20 through each resistor 28, 30, 32, 34 there is a corresponding voltage drop across each resistor (according to V=IR). The voltage drop across each resistor 28, 30, 32, 34 may therefor be predetermined by the voltage output of power source assembly 12 and the resistances chosen for each resistor 24, 28, 30, 32, 34 electrically connected in series thereto.

Figure 3:
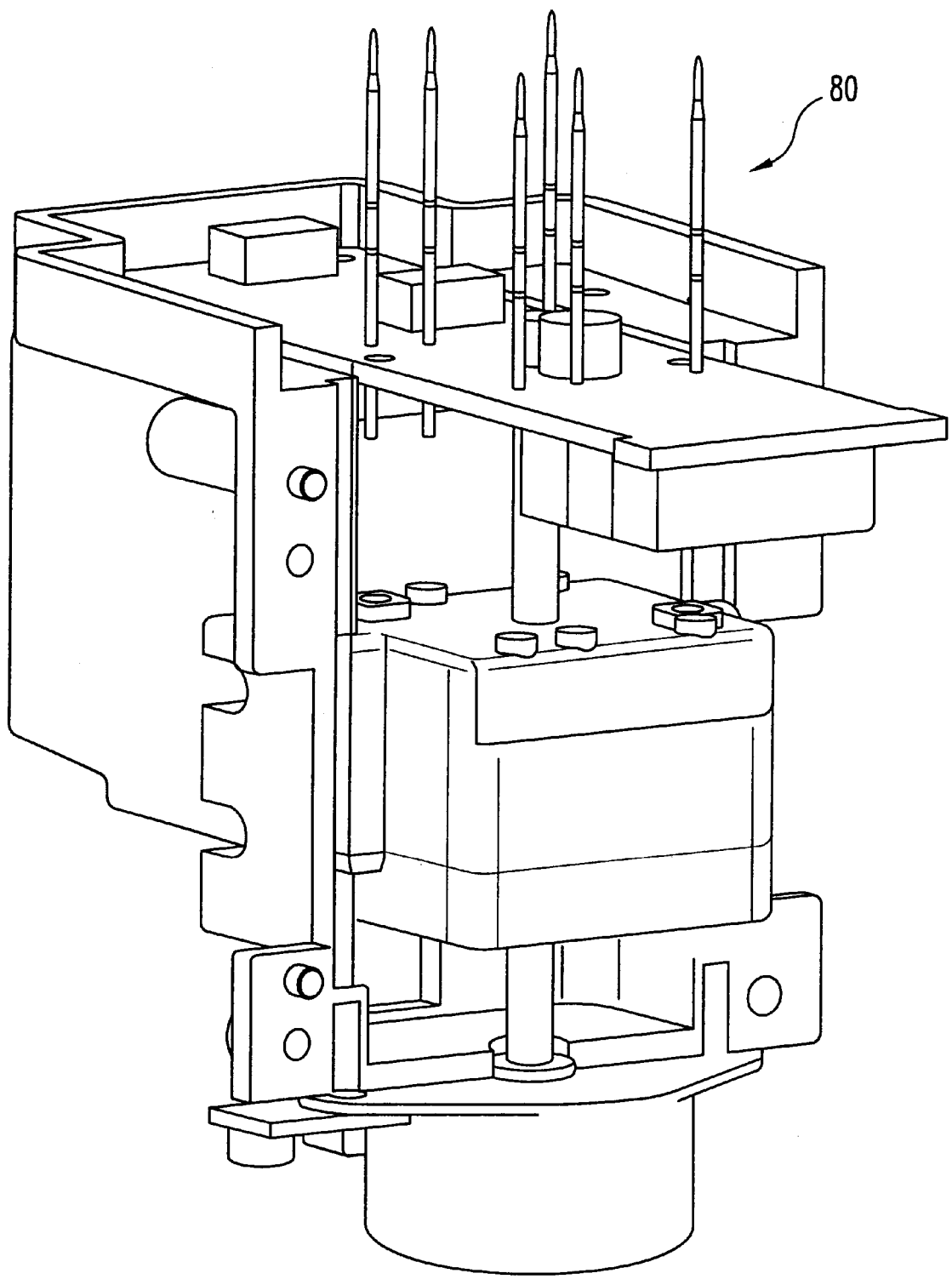
FIG. 3 is a partial view of the probe electrode assembly of a typical electrochemical analysis instrument.

Circuit 10 also includes a connector 40 adapted to receive probe electrodes 80 from an electrochemical analysis device (see FIG. 3) and electrically connect them to circuit 10. Connector 40 includes a plurality of pins for the reception of probe electrodes 80. In this embodiment, connector 40 includes six pins that can be grouped for convenience into three pairs, 42 and 44, 46 and 48, and 50 and 52. Pins 42, 46, and 50 are each electrically connected to a tap point 54 defined as the junction between resistors 30 and 32. Pin 44 is electrically connected through a resistor 60 to a point between resistors 28 and 30. Pin 48 is electrically connected through resistor 64 between resistors 32 and 34. Pin 52 is electrically connected through resistor 62 to a point between battery 20 and resistor 34. The values of resistors 24, 28, 30, 32, 34, 60, 62, and 64 are chosen such that the voltage drops across each pair of pins 42 and 44, 46 and 48, and 50 and 52 are predetermined to be within the measurement range desired to be verified.

A capacitor 70 may also be included in circuit 10, bridging resistors 30, 32 and 34 to further stabilize current flow through circuit 10.

Detailed Circuit Description

The preferred embodiment circuit 10 is described in detail hereinbelow. A battery 20 is provided as a voltage source and includes battery terminals 20A and 20B. Battery 20 is electrically connected to switch 22. Switch 22 has an open position in which current is prevented from flowing therethrough, and a closed position allowing current to flow therethrough. Switch 22 includes two switch terminals, 22A and 22B, with switch terminal 22B electrically connected to battery terminal 20A. Switch terminal 22A is electrically connected to resistor 24 at resistor terminal 24A. Resistor 24 also includes resistor terminal 24B. Diode 26 is connected in parallel with battery 20, switch 22 and resistor 24. Diode terminal 26A is electrically connected to resistor terminal 24B while diode terminal 26B is electrically connected to battery terminal 20B.

Resistors 28, 30, 32, and 34 are electrically connected to receive current from battery 20 when switch 22 is closed. Each resistor 28, 30, 32, and 34 has two resistor terminals, 28A and 28b, 30A and 30B, 32A and 32B, and 34A and 34B, respectively. In particular, resistor terminal 28A is electrically connected to resistor terminal 24B. Resistor terminal 28B is electrically connected to resistor terminal 30A. Resistor terminal 30B is electrically connected to resistor terminal 32A. Resistor terminal 32B is electrically connected to resistor terminal 34A. Resistor terminal 34B is electrically connected to battery terminal 20B. Tap point 54 is defined as the electric connection between resistor terminals 30B and 32A.

Connector 40 includes a plurality of pins for the reception of probe electrodes. Connector 40 includes six pogo pins 42, 44, 46, 48, 50, and 52. Pins 42, 46, and 50 are each electrically connected to tap point 54. Pin 44 is electrically connected to resistor 60 at second resistor terminal 60B. Resistor terminal 60A is electrically connected to resistor terminals 28B and 30A. Pin 48 is electrically connected to resistor terminal 64B. Resistor terminal 64A is electrically connected to resistor terminal 34B. Pin 52 is electrically connected to resistor terminal 62B. Resistor terminal 62A is electrically connected to resistor terminals 32B and 34A. In this embodiment, the resistor values are chosen as follows: resistor 24 has a resistance of 82.5K Ohms, resistor 28 has a resistance of 392K Ohms, resistor 30 has a resistance of 10.5K Ohms, resistor 32 has a resistance of 845 Ohms, resistor 34 has a resistance of 11.3K Ohms, resistor 60 has a resistance of 100K Ohms, 62 resistor 62 has a resistance of 20M Ohms, and resistor 64 has a resistance of 20M Ohms.

Capacitor 70 is connected at capacitor terminal 70A to resistor terminal 28B and at capacitor terminal 70B to diode 26 terminal 26B. Capacitor 70 has a capacitance of 0.022 Farads.

METHOD OF VERIFYING INSTRUMENT FUNCTION

Referring back to FIG. 1, to verify the proper functioning of an electrochemical analysis instrument, dry control cartridge 5 containing test circuit 10 is loaded into the instrument such that electrodes 80 (see FIG. 3) operationally engage connector pins 42, 44, 46, 48, 50 and 52. Dry control cartridge 5 supplies several test voltages and impedances to the instrument, preferably by providing a different voltage and impedance to each pair of connector pins 42–44, 46–48, and 50–52. Test voltages and impedances are supplied to the instrument when switch 22 is closed. Switch 22 must be closed before cartridge 5 may supply voltages to the instrument, so as to conserve power (and operational lifetime) of battery 20. In the preferred embodiment, pogo pins 42–52 yield under pressure from electrodes 80, thereby maintaining even pressure contact on all pins, regardless of alignment differences. The analysis instrument then measures the potentials and impedances between each pair of connector pins 42, 44, 46, 48, 50 and 52. The measured values are compared to the expected or known voltages and impedances supplied by dry test cartridge 5. In the event that the expected and measured values do not substantially match, the instrument can be troubleshot and repaired.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are to be desired to be protected.

What is claimed is:

1. An electric circuit for providing a plurality of voltage and impedance values, comprising:
   a connector having a first connector terminal, a second connector terminal, a third connector terminal, a fourth connector terminal, a fifth connector terminal, and a sixth connector terminal;
   a battery having a first battery terminal and a second battery terminal;
   a switch having a first switch terminal electrically connected to the first battery terminal and having a second switch terminal;
   a first resistor having a first first resistor terminal electrically connected to the second switch terminal and having a second first resistor terminal;
   a diode having a first diode terminal electrically connected to the second first resistor terminal and having a second diode terminal electrically connected to the second battery terminal;
   a capacitor having a first capacitor terminal and having a second capacitor terminal electrically connected to the second battery terminal;
   a second resistor having a first second resistor terminal electrically connected to the second first resistor terminal, and having a second second resistor terminal;
   a third resistor having a first third resistor terminal electrically connected to the second second resistor terminal, and having second third resistor terminal;
   a fourth resistor having a first fourth resistor terminal electrically connected to the second third resistor terminal, and having a second fourth resistor terminal;
   a fifth resistor having a first fifth resistor terminal electrically connected to the second fourth resistor terminal, and having a second fifth resistor terminal electrically connected to the second capacitor terminal, the second diode terminal, and the second battery terminal;
   a sixth resistor having a first sixth resistor terminal electrically connected to the second second resistor terminal, and having a second sixth resistor terminal electrically connected to the second connector terminal;
   a seventh resistor having a first seventh resistor terminal electrically connected to the second fourth resistor terminal, and having a second seventh resistor terminal electrically connected to the fourth connector terminal;
   an eighth resistor having a first eighth resistor terminal electrically connected to the first fifth resistor terminal, the second capacitor terminal, the second diode terminal, and the second battery terminal, and having a second eighth resistor terminal electrically connected to the sixth connector terminal;
   wherein the first, third, and fifth connector terminals are electrically connected to each other and to the second third resistor terminal and the first fourth resistor terminal.

2. The electric circuit of claim 1, wherein the first resistor has a resistance of about 82.5K Ohms, wherein the second resistor has a resistance of about 392K Ohms, wherein the third resistor has a resistance of about 10.5K Ohms, wherein the fourth resistor has a resistance of about 845 Ohms, wherein the fifth resistor has a resistance of about 11.3K Ohms, wherein the sixth resistor has a resistance of about 100K Ohms, wherein the seventh resistor has a resistance of about 20M Ohms, wherein the eighth resistor has a resistance of about 20M Ohms, and wherein the capacitor has a capacitance of about 0.022 Farads.

3. The electric circuit of claim 1 wherein the connector terminals are pogo pins.

4. An electrochemical dry control device, comprising:
   a cartridge;
   a primary electrical circuit operationally connected within the cartridge and further comprising:
     a battery having a first battery terminal and a second battery terminal;
     a first resistor having a first first resistor terminal electrically connected to the first battery terminal and having a second first resistor terminal;
     a second resistor having a first second resistor terminal electrically connected to the second first resistor terminal and having a second second resistor terminal;
     a tap point connected to the second second resistor terminal;
     a third resistor having a first third resistor terminal electrically connected to the tap point and having a second third resistor terminal; and
     a fourth resistor having a first fourth resistor terminal electrically connected to the second third resistor terminal and having a second fourth resistor terminal;
     a fifth resistor having a first fifth resistor terminal electrically connected to the second first resistor terminal and to the first second resistor terminal and having a second resistor terminal;
     a sixth resistor having a first sixth resistor terminal electrically connected to the second third resistor terminal and to the first fourth resistor terminal and having a second sixth resistor terminal;
     a seventh resistor having a first seventh resistor terminal electrically connected to the second fourth resistor terminal and having a second seventh resistor terminal; and a connector operationally connected to the cartridge and further comprising:
   a first pin electrically connected to the tap point;
   a second pin electrically connected to the second fifth resistor terminal;
   a third pin electrically connected to the tap point;
   a fourth pin electrically connected to the second sixth resistor terminal;
   a fifth pin electrically connected to the tap point; and
   a sixth pin electrically connected to the second seventh resistor terminal.

5. The primary electrical circuit of claim 4, further including a switch electrically connected between the battery and the first resistor.

6. The primary electrical circuit of claim 4, further including an eighth resistor electrically connected between the battery and the first resistor.

7. The primary electrical circuit of claim 4, further including a diode operationally connected to the battery and to the first resistor.

8. The device of claim 4, further including a capacitor having a first capacitor terminal connected to the second battery terminal and a second capacitor terminal connected to the first fifth resistor terminal.

9. An electrochemical dry control cartridge for providing a plurality of voltage and impedance inputs to an electrochemical analysis instrument, comprising:
   a connector having a plurality of pairs of pins, wherein each pair of pins is maintained at predetermined voltage potential difference relative to one another; and
   an electric circuit including:
      a battery; and
      a plurality of resistors electrically connected in series with the battery;
      wherein each pair of pins is electrically connected to the battery with at least one resistor electrically connected therebetween.

10. An electric circuit for providing a plurality of voltage and impedance inputs to an electrochemistry instrument, comprising:
   a power source having a first power source terminal and a second power source terminal;
   a first resistor having a first first resistor terminal electrically connected to the first power source terminal and having a second first resistor terminal;
   a second resistor having a first second resistor terminal electrically connected to the second first resistor terminal and having a second second resistor terminal;
   a tap point connected to the second second resistor terminal;
   a third resistor having a first third resistor terminal electrically connected to the tap point and having a second third resistor terminal; and
   a fourth resistor having a first fourth resistor terminal electrically connected to the second third resistor terminal and having a second fourth resistor terminal;
   a fifth resistor having a first fifth resistor terminal electrically connected to the second first resistor terminal and to the first second resistor terminal and having a second resistor terminal;
   a sixth resistor having a first sixth resistor terminal electrically connected to the second third resistor terminal and to the first fourth resistor terminal and having a second sixth resistor terminal;
   a seventh resistor having a first seventh resistor terminal electrically connected to the second fourth resistor terminal and having a second seventh resistor terminal;
   a connector further including:
      a first pin electrically connected to the tap point;
      a second pin electrically connected to the second fifth resistor terminal;
      a third pin electrically connected to the tap point;
      a fourth pin electrically connected to the second sixth resistor terminal;
      a fifth pin electrically connected to the tap point; and
      a sixth pin electrically connected to the second seventh resistor terminal.

11. The circuit of claim 10 wherein the power source is rectified AC current.

12. The circuit of claim 10 wherein the power source is a battery.

13. An electric circuit for providing a plurality of voltage and impedance values, comprising:
   a power source assembly including a power source and a first resistor operationally connected in series;
   a resistor set operationally connected to the power source assembly, including a second resistor, a third resistor, a fourth resistor and a fifth resistor connected sequentially in series;
   a connector having a first connector terminal, a second connector terminal, a third connector terminal, a fourth connector terminal, a fifth connector terminal, and a sixth connector terminal, wherein the first, third, and fifth connector terminals are operationally connected between the third resistor and the fourth resistor;
   a sixth resistor operationally connected to the second connector terminal and operationally connected between the second resistor and the third resistor;
   a seventh resistor operationally connected to the fourth connector terminal and operationally connected between the fourth resistor and the fifth resistor; and
   an eighth resistor operationally connected to the sixth connector terminal and operationally connected between the fifth resistor and the power source.

14. The electric circuit of claim 13, further including a diode operationally connected to the power source assembly.

15. The electric circuit of claim 13, further including a switch operationally connected to the power source assembly.

16. The electric circuit of claim 13, further including a capacitor operationally connected to the power source assembly and to the resistor set.

* * * * *